(12) United States Patent
Asaoka

(10) Patent No.: US 8,752,441 B2
(45) Date of Patent: Jun. 17, 2014

(54) METHOD FOR ASSESSING THE DAMAGE OF KERATIN FIBERS

(75) Inventor: Sachiko Asaoka, Ashiya (JP)

(73) Assignee: The Procter & Gamble Company, Cincinnati, OH (US)

( * ) Notice: Subject to any disclaimer, the term of this patent is extended or adjusted under 35 U.S.C. 154(b) by 463 days.

(21) Appl. No.: 13/038,593

(22) Filed: Mar. 2, 2011

(65) Prior Publication Data

US 2011/0218941 A1    Sep. 8, 2011

Related U.S. Application Data

(60) Provisional application No. 61/309,457, filed on Mar. 2, 2010.

(51) Int. Cl.
*G01N 33/00* (2006.01)

(52) U.S. Cl.
USPC .......................................................... 73/866

(58) Field of Classification Search
USPC .......................................................... 73/866
See application file for complete search history.

(56) References Cited

U.S. PATENT DOCUMENTS

| | | | |
|---|---|---|---|
| 4,510,250 A | | 4/1985 | Kabacoff |
| 4,665,741 A | * | 5/1987 | Kabacoff et al. ............... 73/149 |
| 4,972,718 A | | 11/1990 | Said |
| 5,461,925 A | | 10/1995 | Nguyen |
| 5,915,279 A | * | 6/1999 | Cantrall et al. ................ 73/800 |
| 6,707,929 B2 | | 3/2004 | Marapane |
| 7,749,763 B2 | | 7/2010 | Shmuylovich |
| 2006/0281994 A1 | | 12/2006 | Miyamae |
| 2007/0156345 A1 | | 7/2007 | Hyde |
| 2008/0241854 A1 | * | 10/2008 | Shmuylovich et al. ........ 435/7.1 |
| 2009/0260650 A1 | | 10/2009 | Jung |

FOREIGN PATENT DOCUMENTS

| | | |
|---|---|---|
| AU | 199947482 A1 | 10/2000 |
| EP | 1068861 B1 | 2/2007 |
| EP | 2106749 A1 | 10/2009 |
| JP | 2002014041 A2 | 1/2002 |
| JP | 2005287853 A2 | 10/2005 |
| JP | 2005300241 A2 | 10/2005 |
| JP | 2007263754 A2 | 10/2007 |
| JP | 2008256427 A2 | 10/2008 |
| JP | 2009207697 A2 | 9/2009 |
| KR | 2008067433 A | 7/2008 |
| RU | 2219545 C2 | 12/2003 |
| RU | 2270601 C1 | 2/2006 |
| WO | WO 2007108318 | 9/2007 |

OTHER PUBLICATIONS

C.W.M. Yuen, C.W. Kan, S.Y. Cheng: "Evaluation of Keratin Fibre Damages", Fibers and Polymers, vol. 8, No. 4, 2007, pp. 414-420.
A.C. Santos Nogueira, I. Joekes: "Hair Color Changes and Protein Damage Caused by Ultraviolet Radiation", Journal of Photochemistry and Photobiology, Vvol. 74, May 27, 2004, pp. 109-117.

* cited by examiner

*Primary Examiner* — Peter Macchiarolo
*Assistant Examiner* — Tamiko Bellamy
(74) *Attorney, Agent, or Firm* — Linda M. Sivik

(57) ABSTRACT

Method for assessing damages of keratin fibers using color measurements and area measurements. Said methods are useful for assessing the degree of damages of keratin fibers and also to compare the damages of fibers of different origin, different portions of fibers and/or fibers treated with different cosmetic, chemical and/or mechanical treatments. Said methods are also useful for supporting advertising claims about the efficacy of a treatment.

9 Claims, No Drawings

METHOD FOR ASSESSING THE DAMAGE OF KERATIN FIBERS

CROSS REFERENCE TO RELATED APPLICATIONS

This application claims the benefit of U.S. Provisional Application No. 61/309,457 filed on Mar. 2, 2010.

FIELD OF THE INVENTION

In a first aspect, the present invention relates to a method for assessing damages of keratin fibers using color measurements and area measurements. In a second aspect, the present invention relates to a method for comparing the damages of different keratin fibers using the above method for assessing damages. Said methods are useful for quantitatively and/or qualitatively assessing the degree of damages of keratin fibers and also to compare the damages of fibers of different origin, different portions of fibers and/or fibers treated with different cosmetic, chemical and/or mechanical treatments. Said methods are also useful for supporting advertising claims about the efficacy of a treatment.

BACKGROUND OF THE INVENTION

Keratin fibers, particularly human hair fibers, may be damaged over time. Damages may be caused by environmental factors, including air pollution, sun exposure, water pool, and/or rain. Damages may also be caused by applying to the fibers grooming (cosmetic), chemical and/or mechanical treatments. When hair fibers are damaged, the hair fibers may have undesirable conditions of, for example, "fly-away hair", "split end", and/or color fade.

Assessing the degree of damages caused to hair is of interest in order to understand the impact of various environmental factors as well as the impact of the cosmetic (grooming), chemical and mechanical treatments onto keratin fibers. Such assessment is also of interest in order to demonstrate the efficacy of treatments used for preventing and/or repairing hair damages. Several attempts for assessing hair damages, using different analytical methods, have already been reported. Such attempts include, for example, an assessment using hair volume measurement, and an assessment using hair color measurement. However, such assessments were not enough sensitive to show some differences, for example, efficacy difference among different conditioner products.

There is a need therefore for providing a method for assessing damages of keratin fibers, particularly, human hair fibers. Particularly, there is a need for providing a method for assessing damages of treated keratin fibers using cosmetic, chemical and/or mechanical treatments. In addition, there is also a need for providing a method for assessing and comparing damages of different keratin fibers, e.g. untreated fibers versus treated fibers or fibers treated with different treatments. As far as cosmetic compositions—particularly conditioning compositions—are concerned, there is a need for providing a method for assessing the efficacy of such compositions for preventing and/or repairing damages of hair fibers. There is also a need for providing a method for comparing the efficacy of two or more cosmetic compositions, particularly conditioning compositions, for preventing and/or treating damages of hair fibers. Finally, there is a need for providing a method for supporting advertising claims about the efficacy of a composition—or about the superiority of this composition versus a comparative composition—for preventing and/or repairing damages of hair fibers.

SUMMARY OF THE INVENTION

The present invention relates to a method for assessing damages of keratin fibers comprising the steps of:
providing at least one sample of keratin fiber(s);
measuring a color of a selected portion of the sample and providing a color value;
measuring an area of the selected portion of the sample and providing an area value;
providing a damage value by dividing the color value by the area value.

The present invention also relates to a method for assessing and comparing damages of different keratin fibers comprising the steps of:
providing at least two different samples of keratin fiber(s);
measuring a color of a selected portion of each sample and providing a color value of each sample;
measuring an area of the selected portion of each sample and providing an area value of each sample;
providing a damage value of each sample by dividing the color value by the area value;
comparing the damage value of the samples.

DETAILED DESCRIPTION OF THE INVENTION

In a first aspect, the present invention relates to a method for assessing damages of keratin fibers, by the combination of fiber area measurement and fiber color measurement.

In another aspect, the present invention relates to a method for comparing damages of different keratin fibers by using the above method.

The inventors have surprisingly found that, by the combination of fiber area measurement and fiber color measurement, the method of the present invention provides improved sensitivity of damage assessment of keratin fibers.

Keratin Fiber Sample

The method, according to the invention, comprises the provision of at least one sample of keratin fiber(s) (so-called "provision step"). Said sample may comprise from about 500 fibers to about 150,000 fibers, preferably from about 800 fibers to about 100,000 fibers, more preferably from about 1,000 fibers to about 30,000 fibers. Said fibers may be bundled to each other such that the bundle has at least one free end. One sample usually comprises fibers of the same origin (e.g. from the same person and the same region of the body), and/or of the same portion (e.g. root end or tip end of hair fibers), and/or having been subjected to the same cosmetic, chemical and/or mechanical treatments. When providing at least two, preferably from two to four, more preferably two, different samples of keratin fiber(s), "different samples" means samples differing from each other by the origin of the fibers, the portion of the fibers and/or the treatment(s) applied to fibers.

The fibers may be of sufficient length for the damage assessment method of the present invention which contains both hair color measurement and hair area measurement. The fibers have preferably a length of 3 cm to 30 cm, more preferably of 5 cm to 25 cm, still more preferably of 5 cm to 10 cm. When fibers are bundled to each other, it is preferred that the fibers have the above length from the point to be bundled.

The fibers may be selected from mammal hair, preferably from human hair, more preferably from human female hair. The origin of the human hair may be Caucasian, African, Asian, or any other origin.

The hair fiber may be obtained from any part of the body, e.g. the legs, the arms, the torso, the face or the scalp. The hair fiber is preferably obtained from the scalp.

When the fibers are mammal hair, the damage assessment of the present invention can be done in vivo, using mammal hairs as hair samples without cutting.

A selected portion of fiber sample is used for the damage assessment method of the present invention. Any portion can be used, and fiber end tip portion may be preferred in view of understanding damage degree as well as understanding efficacy of treatments when used.

Color measurement and area measurement can be done by based on the image taken for the selected portion. When using fiber end tip portion for the measurements, the image can be taken from the bottom side of the fiber sample.

Other details of the color measurement and area measurement are described below.

Color and Area Measurements

The damage assessment method of the present invention contains the step of color measurement, i.e., the step of measuring a color of a selected portion of the sample and providing a color value.

The damage assessment method of the present invention also contains the step of area measurement, i.e., the step of measuring an area of the selected portion of the sample and providing an area value.

The color measurement and the area measurement can be done based on an image of the selected portion of the sample.

The color and area measurements can be done, for example, by the following method and equipment:

1. Use a color measurement system comprising: 1) a lighting box, 2) a computer, 3) a camera, 4) a software for image analysis, 5) a sample holder.
2. The lighting box comprises at least one light, preferably a standard day light such as D65 standard lighting source inside. Such lights are placed to illuminate at least the selected portion of the sample which portion is the subject area of the measurement. Preferably, two standard day lights can be installed on left and right top of the lighting box. Such lights are switched on. Preferably, a diffuser is placed to cover the lights.
3. Turn on all instruments: lighting box, computer, a camera preferably digital camera.
4. Lay a white balance checker such as GregtagMacbeth white balance checker at a certain position in the lighting box, and execute white balance.
5. Place a sample with a sample holder in the lighting box such that the hair sample portion to be measured is positioned toward to a camera.
6. Place a color checker chart such as GregtagMacbeth color checker that is a color standard for calibration next to the sample holder.
7. Take an image of the sample, especially the selected portion by a camera. The camera can have autofocus function and can be controlled by a camera remote control software.
8. The image is filed as "raw data file of image before correction (RAW)".
9. The image of the sample can be taken a few times per sample to obtain an average color value.
10. Convert all the RAW files ("raw data file of image before correction (RAW)") to an image file such as TIFF files "Tagged Image File Format (TIFF)" "Joint Photographic Experts Group (JPEG)" by a software. TIFF files are preferred in view of higher sensitivity of the image.
11. A software for image analysis such as LabView (National Instrument Co) and Image ProPlus (Media Cybernetics Inc.) is used hereinafter. Open the TIFF image file and get white balance using a white balance color checker chart such like a GregtagMacbeth color checker chart
12. Then, select the "gray standard" chip on the color checker chart to do the color calibration of the image. Next, select a portion of the sample in the image for the measurement. Such portions are preferably, tip portion especially when the sample comprises a human hair.
13. Compare the brightness to the gray standard and extract the pixels that have lower value than a gray scale. The color value is the integrated area of pixels that has lower than threshold of brightness (gray scale: e.g. 200 for Caucasian hair) in the selected portion.
14. Within the selected area of the above 12, extract the pixels that gray scale larger than white calibration standard. The area value is calculated by integrating all pixel areas that gray scale larger than gray scale standard (e.g. 255 for Caucasian hair).

Damage Value

The damage assessment method of the present invention contains the step of providing a damage value by dividing the color value by the area value. Sample having a bigger damage value is considered to be more damaged.

Treatment

The method may also comprise the step of treating the sample (so-called "treatment step"). The treatment step is preferably carried out after the provision step and before the tagging step. The treatment step may be carried out by treating the sample using any suitable cosmetic composition, chemical and/or mechanical treatment.

This step may be carried out by applying a cosmetic composition onto keratin fiber. Any suitable cosmetic composition known in the art may be used such as shampoos, conditioning compositions, hair rinse-off treatments, hair leave-on treatments, styling compositions. For example, any commercially available shampoos, conditioners, hair rinse-off treatments and hair leave-on treatments of tradename Pantene® and Head & Shoulders® may be used.

Only one composition may be applied onto fibers. Alternatively, two or several compositions may be applied simultaneously or sequentially. In addition, before and/or after applying each composition, the fibers may further be wetted, rinsed and/or dried. In one embodiment, the treating step comprises treating (washing) the fibers with a shampoo, then rinsing the washed fibers with water, then drying the fibers. In another embodiment, the treating step comprises treating (washing) the fibers with a shampoo, then rinsing the washed fibers with water, then treating the fibers with a conditioning composition, then rinsing the treated fibers with water, then drying the fibers. In another embodiment, the treating step comprises treating (washing) the fibers with a shampoo, then rinsing the washed fibers with water, then treating the fibers with a conditioning composition, then rinsing the treated fibers with water, then treating at least one time the fibers with a hair rinse-off treatment, then rinsing the treated fibers with water, then drying the fibers.

Alternatively or complementary, this step may be carried out by chemically treating the fibers using a chemical treatment. Any suitable chemical treatment known in the art may be used such as permanent waving treatment, bleaching treatment and/or color-dyeing treatment.

Alternatively or complementary, this step may be carried out by mechanically treating the fibers. Any suitable mechanical treatment known in the art may be used such as brushing, combing, towel rubbing, and/or blow drying.

Comparison

The method may also comprise the step of comparing damage values of the samples (so-called "comparison step").

When providing at least two samples,

In one embodiment, one sample may comprise the tip portion of fibers and the other sample may comprise the root portion of the same fibers. Providing and comparing different portions of the same fibers, particularly tip versus root, allows assessing the difference of the degree of damages over time, as the fibers grow.

The comparison step is also beneficial for comparing the effects of one treatment onto fibers versus no treatment. In one embodiment, one sample may comprise untreated fibers and the other sample comprises fibers treated with a cosmetic composition. The other sample may be treated with a shampoo, and/or a conditioning composition, and/or a hair rinse-off treatment, and/or a leave-on treatment, and/or any other suitable cosmetic composition. Comparing treated fiber(s) and untreated fiber(s) is beneficial for assessing the damaging effects of the compositions such as shampoos onto hair or, in contrast, for assessing the benefits of the compositions such as conditioning compositions for preventing and/or repairing the damages of the fiber(s).

The comparison step is further beneficial for comparing the efficacy of at least two different treatments for preventing and/or repairing the damages of fibers. In one embodiment, the samples may be treated with different cosmetic compositions. For example and non-exhaustively, (1) one sample may be treated with one shampoo and the other sample with another shampoo; (2) one sample may be treated with one shampoo and the other sample may be treated with the same shampoo and then one conditioner; (3) one sample may be treated with one shampoo and then one conditioner and the other sample may be treated with the same shampoo and then another conditioner, (4) one sample may be treated with one shampoo and then one conditioner and the other sample may be treated with the same shampoo, then the same conditioner, and then a rinse-off treatment, (5) one sample may be treated with one shampoo and then one conditioner and the other sample may be treated with the same shampoo, then the same conditioner, and then a leave-on treatment, (6) one sample may be treated with one shampoo and then one conditioner and the other sample may be treated with another shampoo and then the same conditioner; (7) one sample may be treated one time with one shampoo and the other sample may be treated two or several time with the same shampoo; (8) one sample may be treated one time with one conditioner and the other sample may be treated two or several times with the same conditioner. Comparing differently treated fiber(s) is beneficial for comparing the damaging effects of different shampoos (see (1)); for assessing the mitigating effects of conditioners onto shampoo treatments (see (2)); for comparing the benefits of conditioning compositions for preventing and/or repairing the damages of the fiber(s) (see (3)); for assessing the mitigating effects of rinse-off treatments onto shampoo treatments (see (4)); for assessing the mitigating effects of leave-on treatments onto shampoo treatments (see (5)); for comparing the mitigating effects of one conditioners onto different shampoo treatments (see (6)); for comparing the effects of repeating treatments onto fiber(s) (see (7) and (8)).

The comparison step is beneficial for example for comparing the effects of chemical and/or mechanical treatments. For example, in one embodiment, one sample may comprise untreated fiber(s) and the other sample comprises fibers being chemically-treated. Alternatively, the samples may comprise fiber(s) be treated with different chemical treatments. In another embodiment, one sample may comprise untreated fiber(s) and the other sample comprises fibers being mechanically-treated. Alternatively, the samples may comprise fiber(s) be treated with different mechanical treatments.

Advertisement Support

The method may also comprise the step of utilizing said assessment to support advertising claims (so-called "advertising step"). Making advertising steps based on the outcome of the comparison between two different samples is beneficial for example for advertising the efficacy of a treatment for preventing and/or repairing damages to fibers and/or for advertising the superiority of one treatment versus another treatment for preventing and/or repairing damages. When advertising one treatment (e.g. a conditioning composition) versus another one, the data and/or the pictures obtained using this method may be used therefore support and/or demonstrate advertising claims according to which said treatment provide higher performance versus the other one for preventing and/or repairing fiber damages.

EXAMPLE

Materials

Sample: 15 cm long, a bundle of about 3,300 hair fibers of Caucasian female. Shampoo composition of pH=5-7 comprising Sodium laureth sulfate (6.0%), Sodium lauryl sulfate (6.0%), cocamidopropyl betaine (1%), cocamide MEA (0.85%), Glycol Disterate (1.5%), Guar Hydroxypropyltrimonium Chloride (0.4%), Dimethicone (3%), preservatives (0.6%), water q.s. to 100%.

Conditioning composition: composition of pH=5-7 comprising behentrimonium methosulfate/isopropyl alcohol (2.8%), fatty alcohols (6.5%), terminal aminodimethicone (2%), preservatives (0.6%), water q.s. to 100%.

Percentages of compounds are weight percent per total weight of the composition

Protocol

Depending on the method carried out, some of the steps may be omitted, e.g. the treating step.

1. Treatment Step

The samples are treated by applying a shampoo, then, if necessary, a conditioning composition, as described below. These samples are hereinafter referred to as "treated samples".

1.1. Hang a sample on bar
1.2. Wet the sample 15 seconds and squeeze the sample to remove excess water
1.3. Apply shampoo product 0.2 ml the sample and milk for 30 seconds
1.4. Rinse the sample for 30 seconds
1.5. Repeat 1.3.-1.4. protocol
1.6. When conditioner is applied, apply conditioner 0.2 ml the sample and milk for 30 seconds
1.7. When conditioner is applied, rinse the sample for 30 seconds
1.8. Leave the sample in the control humidity and temperature (Humidity 45%, Temperature 21° C.) for one night.

2. Combing Step 2.1. Hang the treated sample in the machine. (make sure hair insert into combs properly, not only surface combing)
2.2. Comb the first side of the sample for 12 cycles (14-15 cycles/min)
2.3. Turn the sample to the other side, comb the sample for 13 cycles (14-15 cycles/min)
2.4. Repeat steps 2.2. and 2.3. three times
2.5. Keep hang switches in control humidity and temperature Humidity 45%, Temperature 21° C. for at least one night.

3. Measurement:
3.1. Use a color measurement system comprising: 1) a lighting box, 2) a computer, 3) a camera, 4) a software for image analysis, 5) a sample holder.
3.2. The lighting box comprises two D65 standard lighting sources which are installed on left and right top of the lighting box. A diffuser is placed to cover the lights. Nikon D2Xs digital camera is also installed on the top of the lighting box.
3.3. Turn on all instruments: lighting sources, computer, and the digital camera.
3.4. Lay GretaMcbeth white balance checker at a certain position in the lighting box, and execute white balance.
3.5. Place the hair sample with a sample holder in the lighting box such that the tips of the hair are toward to the digital camera installed at the top of the lighting box. The hair sample is held at the position of 2 cm from the tips.
3.6. Place GretaMcbeth color checker next to the sample holder.
3.7. Take an image of the sample by the camera by a remote control software and with autofocus function.
3.8. The image is filed as "raw data file of image before correction (RAW)".
3.9. The image of the sample can be taken a few times per sample to obtain an average color value.
3.10. Convert all the RAW files to TIFF files.
3.11. A software for image analysis Image ProPlus (Media Cybernetics Inc.) is used hereinafter. Open the TIFF image file and get white balance using GretaMcbeth color checker chart.
3.12. Then, select the "gray standard" L20 chip on the color checker chart to do the color calibration of the image. Next, select a tip portion of the sample in the image for the measurement.
3.13. Compare the brightness to the gray standard and extract the pixels that have lower value than a gray scale. The color value is the integrated area of pixels that has lower than threshold of brightness (gray scale: 200) in the selected portion.
3.14. Within the selected area of the above 15, extract the pixels that gray scale larger than white calibration standard. The area value is calculated by integrating all pixel areas that gray scale larger than gray scale standard (255).
3.15. Damage value is calculated by dividing the color value by the area value.

Assessment and Comparison of Damages of Fiber that Differently-Treated Tip Portions of Hair One sample is provided. The sample is first treated by Shampoo only, and then treated together with Conditioner. Detailed Shampoo and Conditioner formulations and detailed methods of treatment and measurement are described above.

|  | Shampoo + Conditioner | Shampoo only |
| --- | --- | --- |
| Damage value | 106 | 113 |

As shown by the data provided in the above table, the damage value of the sample treated by both shampoo and conditioner is significantly lower than that of the sample treated by shampoo only (with One way ANOVA @95% confidence level).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assessing damages of keratin fibers comprising the steps of:
   providing at least one sample of keratin fiber(s);
   measuring a color of a selected portion of the sample and providing a color value;
   measuring an area of the selected portion of the sample and providing an area value;
   providing a damage value by dividing the color value by the area value;
   wherein the method further comprises the step of taking an image of the selected portion of the sample, and wherein the color measurement and area measurement are made based the image;
   wherein color value is the integrated area of pixels that has lower than threshold of brightness (gray scale) in the selected portion, and wherein area value is calculated by integrating all pixel areas that gray scale larger than gray scale standard.

2. The method, according to claim 1, wherein the keratin fiber is human hair.

3. The method of claim 1, wherein the selected portion is an end tip of the sample 4. The method of claim 1, wherein the selected portion is end tip of the sample, and wherein the image is taken from the bottom side of the sample.

5. A method for assessing and comparing damages of different keratin fibers comprising the steps of:
   providing at least two different samples of keratin fiber(s);
   measuring a color of a selected portion of each sample and providing a color value of each sample;
   measuring an area of the selected portion of each sample and providing an area value of each sample;
   providing a damage value of each sample by dividing the color value by the area value;
   comparing the damage value of the samples;
   wherein the method further comprises the step of taking an image of the selected portion of the sample, and wherein the color measurement and area measurement are made based the image;
   wherein color value is the integrated area of pixels that has lower than threshold of brightness (gray scale) in the selected portion, and wherein area value is calculated by integrating all pixel areas that gray scale larger than gray scale standard.

6. The method of claim 5, wherein the samples differ from each other by the origin of the fibers, the portion of the fibers and/or the treatment(s) applied to the fibers.

7. The method of claim 5, wherein one sample comprises untreated fiber(s) and the other sample comprises fiber(s) treated with a cosmetic, chemical and/or mechanical composition(s).

8. The method of claim 5, wherein the samples are treated with different cosmetic, chemical, and/or mechanical treatments.

9. The method of claim 7 or claim 8, further comprising the step of utilizing said comparison to support advertising claims about the efficacy of a treatment.

* * * * *